United States Patent [19]

Fox, Jr. et al.

[11] 4,404,197

[45] Sep. 13, 1983

[54] ANTIMICROBIAL COMPOSITIONS CONTAINING 1-ETHYL-6-FLUORO-1,4-DIHYDRO-4-DIHYDRO-4-OXO-7-(1-PIPERAZINYL)-3-QUINOLINE CARBOXYLIC ACID OR METAL SALTS THEREOF AND SILVER SULFADIAZINE

[76] Inventors: Charles L. Fox, Jr., Saw Mill Rd., Sherman, Conn. 06784; Shanta M. Modak, 184 Howland Ave., River Edge, N.J. 07661

[21] Appl. No.: 264,096

[22] Filed: May 15, 1981

[51] Int. Cl.³ ............................................. A61K 31/625
[52] U.S. Cl. ................................. 424/229; 424/245; 424/250
[58] Field of Search ...................... 424/229, 250, 245

[56] References Cited

U.S. PATENT DOCUMENTS 3,761,590  9/1973  Fox ...................................... 424/228
4,146,719  3/1979  Irikura ................................. 544/363

*Primary Examiner*—Leonard Schenkman
*Attorney, Agent, or Firm*—Scully, Scott, Murphy & Presser

[57] ABSTRACT

Compositions which include 1-ethyl-6-fluoro-1,4-dihydro-4-oxo-7-(1-piperazinyl)-3-quinoline carboxylic acid or its metal salts, e.g., silver, zinc, cobalt or cerium salts, and silver sulfadiazine are effective in the treatment of burns. Of special interest are compositions containing silver sulfadiazine and the silver salt of the above-identified quinoline carboxylic acid, wherein even though each compound is present in a concentration which would be ineffective if either compound were present alone, the resulting compositions are effective. The compositions of this invention may be applied to the affected surface of a burn victim either directly or in combination with a physiologically acceptable carrier, such as a water-dispersible, hydrophilic carrier.

2 Claims, No Drawings

ANTIMICROBIAL COMPOSITIONS CONTAINING 1-ETHYL-6-FLUORO-1,4-DIHYDRO-4-DIHYDRO-4-OXO-7-(1-PIPERAZINYL)-3-QUINOLINE CARBOXYLIC ACID OR METAL SALTS THEREOF AND SILVER SULFADIAZINE

BACKGROUND OF THE INVENTION

Despite the development of effective topical and systemic antibiotics, invasive wound sepsis and septicemia from Pseudomonas aeruginosa remain problems in seriously burned patients. Emergence and development of drug resistant species of bacteria have defied the control obtained through the regimen of potent antibiotics. In recent years, numerous reports of gentamicin resistant gram negative organisms (Shulman, J. A., Terry, P. M., Hough, C. E.: Colonization with a gentamicin resistanct Pseudomonas aeruginosa pyocine type 5 in a burn unit. J. of Inf. Diseases 124:S18, 1971), especially Pseudomonas, have appeared in the literature. (Snelling, C. F. T., Ronald, A. R., Cates, C. Y., et al.: Resistance of gram negative bacilli to gentamicin, J. of Inf. Diseases 124:S264, 1971; Chadwick, P.: Resistance of Pseudomonas aeruginosa to gentamicin, Canadian Med. Assoc. J. 109:585, 1973; Bryan, L. E., Shahrabadi, M. S., Van Denelzen, H. M.: Gentamicin resistance in Pseudomonas aeruginosa. R-factor mediated resistance, Antimicrobial Agents and Chemotherapy 6:191, 1974). Although silver sulfadiazine (AgSD), presently the most commonly used topical agent in the treatment of burn wound infections (Fox, Jr., C. L.: A new topical therapy for Pseudomonas in burns, Arch. Surg. 96:184, 1968; Fox, Jr., C. L., Rappole, B. W., Stanford, J. W.: Control of Pseudomonas infection in burns by silver sulfadiazine, Surg. Gyn. Obstr. 128:1021, 1969), appeared to surmount these problems, Pseudomonas infections resistant to silver sulfadiazine treatment have been reported recently in burned patients (Gayle, W. E., Mayhall, C. G., Lamb, A., et al.: Resistant enterobacter cloacal in a burn center. The effectiveness of silver sulfadiazine, J. of Trauma 18:327, 1978; Heggers, J. P., Robson, M. C.: The emergence of silver sulfadiazine resistant Pseudomonas aeruginosa, Burns 5:184, 1978).

Similar occurrences of AgSD-resistant Pseudomonas infections in patients have been observed in other parts of the world. Several such resistant strains have been obtained and the nature of their resistance studied in an experimental burn model. This investigation revealed an unusual phenomenon, namely, normal sensitivity of Pseudomonas to AgSD in vitro, but resistance to topical AgSD therapy in infected burn wounds in mice and rats. (Modak, S., Stanford, J. W., Bradshaw, W., Fox, Jr., C. L.: Silver sulfadiazine resistant Pseudomonas infection in experimental burn wounds. 3rd Intrl. Congr. of Pharma. Treatment of Burns, 1980 (in press) ed. Donati, L., Burke, J., Bertelli, A., Italy,)

Comparative studies of the virulence and drug sensitivity of in vivo AgSD sensitive and nonsensitive strains were carried out to investigate the possible mechanism of in vivo resistance. Since all the resistant strains obtained from burn patients appeared to be sensitive in vitro, the evaluation of a topical agent for its effectiveness was determined in experimental burn models. Several other antibacterial agents known to be effective in vitro were also ineffective against these strains.

The continued search for an effective topical agent led to the discovery that 1-ethyl-6-fluoro-1,4-dihydro-4-oxo-7-(1-piperazinyl)-3-quinoline carboxylic acid and metal salts thereof (referred to hereinafter as QC and its metal salts as MeQC) possess high anti-Pseudomonas activity in vitro (Ito, A., Hira, K., Inoue, M., et al.: In vitro antibacterial activity of AM-715, a new nalidixic acid analog, Antimicrobial Agents and Chemotherapy 17:103, 1980, and French patents 879,106 and 870,576), and are effective in controlling AgSD-resistant Pseudomonas infections in burned mice. See also our co-pending U.S. application, Ser. No. 193,307, filed Oct. 2, 1980, the disclosure of which is hereby incorporated by reference into this application. Specifically, that application discloses QC and MeQC, e.g., AgQC, as topical antimicrobials useful in burn therapy.

SUMMARY OF THE INVENTION

It has been found that compositions containing 1-ethyl-6-fluoro-1,4-dihydro-4-oxo-7-(1-piperazinyl)-3-quinoline carboxylic acid (QC) and/or its metal salts (MeQC), such as its zinc salt (ZnQC), cobalt salt (CoQC), cerium salt (CeQC), silver salt (AgQC) and magnesium salt (MgQC), together with silver sulfadiazine (AgSD), provide improved compositions useful in burn therapy and compositions generally useful for combatting topical or surface or skin infections, including microbial and/or fungal infections and the like.

Moreover, it has unexpectedly been found that compositions comprising the silver salt of 1-ethyl-6-fluoro-1,4-dihydro-4-oxo-7-(1-piperazinyl)-3-quinoline carboxylic acid and silver sufadiazine, in which the compounds are present in amounts which would be ineffective if only one of the compounds were present, are useful in the treatment of burns in animal and man. These compositions may be applied to the affected surface or burned surface of a burn victim, either directly, or preferably in the form of a composition which includes a physiologically acceptable carrier, such as a water-dispersible hydrophilic carrier, e.g., an oil-in-water dispersion.

DETAILED DESCRIPTION OF THE INVENTION

1-Ethyl-6-flouro-1,4-dihydro-4-oxo-7-(1-piperazinyl)-3-quinoline carboxylic acid (QC) has the structure:

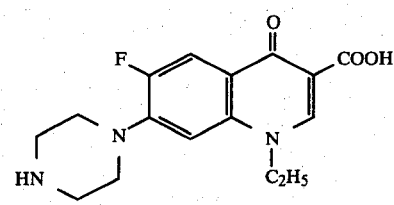

and is known to have antibacterial activity in vitro against standard bacterial strains such as B. subtilis, S. aureus, P. aeruginosa, and E. coli strains. Ito, A. et al., Antimicrobial Agents and Chemotherapy 17:103, 1980, supra. The metal salts of QC, i.e., MeQC, viz. MgQC, CoQC, ZnQC, CeQC, and AgQC are also of interest and appear to be suitable topical antimicrobial agents. For example, AgQC, which would appear to have the structure wherein the COOH moiety of QC is changed to COO$^-$Ag$^+$, is a potent antimicrobial. Unlike certain compounds which have high in vitro antibacterial activity, but are ineffective in controlling silver sulfadiazine-resistant Pseudomonas infections in burned mice, QC and MeQC, are effective in controlling such infections, such as when employed in amounts or concentrations greater than about 5–10 mM, desirably at a concentration greater than 2 mM.

The metal salts of 1-ethyl-6-fluoro-1,4-dihydro-4-oxo-7-(1-piperazinyl)-3-quinoline carboxylic acid, i.e., MeQC, are readily prepared. For example, AgQC may be prepared as follows. QC is obtained directly or synthesized by known techniques. The sodium salt of 1-ethyl-6-fluoro-1,4-dihydro-4-oxo-7-(1-piperazinyl)-3-quinoline carboxylic acid, i.e., NaQC, may then be prepared by adding an equimolar amount of sodium hydroxide to the QC. The silver salt, i.e., AgQC, may be prepared by reacting the NaQC in an aqueous solution with a stoichiometric quantity of a suitable silver salt such as silver nitrate, silver chloride, or the like.

Silver sulfadiazine is well known as an effective agent in burn therapy. However, the silver sulfadiazine must be employed in compositions in amounts or concentrations greater than about 1.0 percent by weight. At lesser amounts, silver sulfadiazine (AgSD) is ineffective.

Not only have combinations of AgSD and QC or MeQC, wherein AgSD is present at a concentration greater than 1% by weight and QC and MeQC are present at a concentration greater than 2 mM, been found to provide potent antimicrobial compositions, but also, it has unexpectedly been found that a synergistic result is obtained when AgSD and AgQC are combined for use in burn treatment. Specifically, compositions useful in burn therapy have been discovered in which the amounts of AgSD and of AgQC are below the amounts required for antibacterial activity or effectiveness if only one of the compounds is present or included.

Thus, compositions useful in burn therapy may be prepared in which the amount or concentration of AgQC is less than about 10 mM, such as an amount from about 1 mM up to about 10 mM, e.g., about 3 mM; and the amount or concentration of AgSD is less than about 1.0 percent by weight, such as an amount from about 10 mM up to about 1.0 percent, e.g., about 30 mM.

The compositions of this invention may be applied directly to the surface of burn wounds or infections, or, preferably, may be employed in combination with a physiologically acceptable carrier. When employed in a composition with a physiologically acceptable carrier, the carrier is desirably a conventional water-dispersible, hydrophilic or oil-in-water carrier, particularly a conventional semi-soft or cream-like, water-dispersible or water-soluble, oil-in-water emulsion, which may be applied to an affected burn surface or infected surface with a minimum of discomfort.

Suitable compositions may be prepared by merely incorporating or homogeneously admixing finely divided compounds with the hydrophilic carrier or base or ointment. One technique in accordance with this invention for incorporating the metal salts, e.g., the silver salt, in a hydrophilic ointment, such as an oil-in-water emulsion, involves reacting equimolar aqueous solutions of silver nitrate and NaQC to yield a white precipitate which is AgQC. The resulting precipitate, after washing and drying, is then mixed or blended with the candidate hydrophilic ointment, such as the oil-in-water emulsion, to yield a composition which includes the silver salt dispersed in the ointment. The AgSD may be incorporated into the composition either together with the AgQC or independently.

Compositions in accordance with this invention containing AgSD and MeQC dispersed in a water-dispersible, hydrophilic carrier or ointment, e.g., a hydrophilic, oil-in-water emulsion, are usually characterized by the following components and amounts by weight set forth in Table I:

TABLE I

| Component | Amount[1] |
|---|---|
| Petrolatum | 0–25 |
| Water-insoluble $C_{16}$–$C_{22}$ fatty alcohol | 7–45 |
| Emollient | 0–15 |
| Emulsifying Agents, preferably non-ionic | 4–16 |
| Humectant | 7–40 |
| AgSD | 10mM–1.0 |
| QC or MeQC | 1mM–10mM |
| Preservative | 0–0.3 |
| Deionized or Distilled Water q.s. | 0–80 |
|  | 100 |

[1]Amounts are in percent by weight unless otherwise indicated.

The fatty alcohols, stearyl alcohol, cetyl alcohol, lauryl alcohol and myristyl alcohol are useful in the preparation of compositions in accordance with this invention. These preferential oil-soluble fatty alcohols act as stiffeners in the resulting compositions. As the emollient, isopropyl myristate, lanolin, lanolin derivatives, isopropyl palmitate, isopropyl stearate and the corresponding sebacates and other known emollients are suitable. As the emulsifying agent sorbitan monooleate, such as an amount in the range 0.5–4 percent by weight, and polyoxyl 40 stearate in an amount in the range 7–12 percent by weight, both non-ionic emulsifying agents, are satisfactory. A suitable humectant would be propylene glycol, sorbitol, or glycerin, or mixtures thereof, all being water-soluble compounds. A suitable preservative would be any of the useful conventional water-soluble preservatives which exhibit anti-microbial activity, such as sorbic acid, benzoic methylparaben, propylparaben, and mixtures thereof.

In the formulation of a composition having the make-up set forth in Table I hereinabove, as the amount of aqueous phase is increased, the solid content, i.e., the water-immiscible or water-insoluble components, e.g., fatty alcohol, such as stearyl alcohol, and/or petrolatum, must also be increased relatively to help stiffen the composition. The preservative, e.g., methylparaben, is employed in the formulation only as a preservative for the overall composition and, as indicated, methylparaben was found to be a satisfactory preservative. Methylparaben, as indicated, however, may also be used in combination with propylparaben.

Accordingly, compositions useful in the practices of this invention would include compositions comprising 0–25 percent by weight petrolatum, 7–45 percent by weight stearyl alcohol, 0–15 percent by weight isopropyl myristate, 5–20 percent by weight of an emulsifying agent, 7–40 percent by weight propylene glycol, 10 mM–1.0 percent by weight AgSD and 1 mM–10 mM of AgQC, the remainder being water, as required, to bring the total percentage to 100 percent. Other useful compositions would include compositions consisting essentially of 3 mM AgQC, 30 mM AgSD, 7–8 percent by weight propylene glycol, 38–44 percent by weight water, 14–18 percent by weight petrolatum, 14–18 percent by weight stearyl alcohol, 5–8 percent by weight isopropyl myristate, 0.5–2 percent by weight sorbitan monooleate and 6–10 percent by weight polyoxyl 40 stearyl. Another composition useful in the practice of this invention would include the composition consisting essentially of 0–25 percent by weight petrolatum, 7–45 percent by weight of an aliphaic fatty alcohol having a carbon atom content in the range $C_{16}$–$C_{22}$, 0–15 percent by weight of an emollient, 7–16 percent by weight of an emulsifying agent, 7–14 percent by weight of a humectant, 3 mM AgQC, and 30 mM AgSD.

Although the preceding discussion has primarily concerned the use of AgSD in combination with QC or MeQC, especially AgQC, it is likely that other metal salts of sulfadiazine may be usefully employed in the practices of this invention. For example, zinc sulfadiazine, cerium suladiazine, and cobalt sulfadiazine are known to be useful as topical antimicrobial agents in the treatment of burn victims. Thus, it may be that combinations of one or more of these compounds with QC or MeQC will provide advantages when employed in burn therapy or the treatment of surface infections.

The results of various experiments illustrating the practices of this invention are now set forth.

EXPERIMENTAL DETAILS

METHODS AND MATERIALS

Bacterial Strains: Ps. Boston was the strain used in our previous investigations (Fox, Jr., C. L., Sampath, A. C., Standford, J. W.: Virulence of pseudomonas infection in burned rats and mice. Arc. Surg. 101:508, 1970); Ps. Mangalore was isolated from a burn patient in Kasturba Medical College, Mangalore, India; Ps. 181 was obtained from Hospital de los Ninos, Lima, Peru, and from Shanghai, China; and AgSD resistant Ps. Boston was produced in our laboratory by repeatedly growing this organism in medium containing increasing amounts of AgSD.

In vitro assay of microbial inhibition: Inhibition indices are obtained by tube dilution tests using nutrient broth. Growth in the presence and absence of drugs was observed by turbidity measurement after incubation at 37° C. for 24–48 hours (Fox, Jr., C. L., Modak, S. M., Stanford, J. W.: Cerium sulfadiazine as a topical agent for burn wound infections: A comparison with silver sulfadiazine and zinc sulfadiazine. Burns 4:233, 1978).

Animal experiments: Mice (female Swiss 18–22 grams) received scalds using methods reported previously (Fox, Jr., C. L.: A new topical therapy for pseudomonas in burns. Arch. Surg. 96:184, 1968; Fox, Jr., C. L., Sampath, A. C., Stanford, J. W.: Virulence of pseudomonas infection in burned rats and mice. Arch. Surg. 101:508, 1970; Fox, Jr., C. L., Modak, S. M., Stanford, J. W.: Cerium sulfadiazine as a topical agent for burn wound infections: A comparison with silver sulfadiazine and zinc sulfadiazine. Burns 4:233, 1978). The wounds were contaminated one hour post burn with freshly prepared 18–20 hour broth culture of pseudomonas diluted to optical density 0.30. Infection was induced by immersing the tail in the culture.

The first treatment was administered 4 hours post infection by rubbing the medicated creams over all burned surfaces. All drugs used were mixed in a cream base such as described hereinabove. Thereafter, all animals were observed and treated once daily. The primary criterion was survival. Animals that succumbed were autoposied and the cardiac blood cultured to verify the presence of pseudomonas.

RESULTS

In vivo efficacy of silver salt 1-ethyl-6-fluoro-1,4-dihydro-4-oxo-7-(1-piperazinyl)-3-quinoline carboxylic acid in combination with silver sulfadiazine In vivo efficacy of the silver salt of the carboxylic acid and of silver sulfadiazine against Ps. Mangalore, Ps. 181, and AgSD-resistant Ps. Boston were tested and compared with that of a combination of both compounds in burned mice. The results are summarized in Table II. After infection with these resistant strains, the mortality with 30 mM silver sulfadiazine therapy was 80 percent by the eighth day post burn. In the groups of mice receiving topical therapy with the silver salt of the carboxylic acid, the mortality was 0 percent for both Ps. Mangalore and Ps. 181 infection when the concentration of the drug in the cream was 10 mM/kg. When lower amounts were used, there was 45–80 percent mortality. The synergistic results obtained when both compounds are present are clearly shown.

TABLE II

Topical Therapy of Burned Mice Infected with AgSD Resistant Pseudomonas

| Groups | No. of Mice | % Mortality (Days Post Burn) | | | | | |
|---|---|---|---|---|---|---|---|
| | | 2 | 3 | 4 | 5 | 6 | 7 | 8 |
| Control | 10 | 40 | 100 | 100 | 100 | 100 | 100 | 100 |
| 30mM AgSD | 10 | 10 | 10 | 30 | 50 | 80 | 80 | 80 |
| 10mM Ag salt | 10 | 0 | 0 | 0 | 0 | 0 | 0 | 0 |
| 6mM Ag salt | 9 | 0 | 10 | 10 | 10 | 10 | 30 | 45 |
| 3mM Ag salt | 5 | 20 | 40 | 40 | 40 | 40 | 80 | 80 |
| 3mM Ag salt + 30mM AgSD | 5 | 0 | 0 | 0 | 0 | 0 | 0 | 0 |

In Vivo Efficacy

Mice anesthetized with ether were given a 30 percent scald by dipping the lower third of their body into a water bath at 68° C. for 7 seconds. One hour post burn, mice were given 1 ml of Normosol by I.P. injection and then infected by dipping the tail in an overnight culture of pseudomonas diluted to 0.30 O.D. at 600 nm.

The animals were divided at random into groups of 5, and topical therapy was initiated 4 hours post infection. Thereafter they were treated once daily. The primary criterion was survival. Animals that succumbed were autopsied and their cardiac blood was cultured to verify the presence of pseudomonas sepsis.

The results were as follows:

| Drug | Cage No. | Ps. Boston infection: Days Post Burn | | | | | | | | | |
|---|---|---|---|---|---|---|---|---|---|---|---|
| | | 2 | | 3 | | 4 | | 6 | | 7–9 | |
| | | Dead | (%) | Dead | (%) | Dead | (%) | Dead | (%) | Dead | (%) |
| Control | 1 | 5 | 0 | (0) | 5 | (100) | 5 | (100) | 5 | (100) | 5 | (100) |
| Topical AgSD (30mM) | 2 | 5 | 0 | (0) | 9 | (0) | 0 | (0) | 2 | (40) | 4 | (80) |

-continued

| | Cage | No. | Dead | (%) | Dead | (%) | Dead | (%) | Dead | (%) | Dead | (%) | Dead | (%) |
|---|---|---|---|---|---|---|---|---|---|---|---|---|---|---|
| 3mM/kg silver carboxylic acid | 3 | 5 | 2 | (40) | 4 | (80) | 5 | (100) | 5 | (100) | 5 | (100) | | |
| 3mM/kg silver salt of carboxylic acid plus AgSD (30mM) | 4 | 5 | 0 | (0) | 0 | (0) | 0 | (0) | 0 | (0) | 0 | (0) | | |

| | | | Ps. Boston and Ps. Mangalore Infection: Days Post Burn | | | | | | | | | | | |
|---|---|---|---|---|---|---|---|---|---|---|---|---|---|---|
| | | | 2 | | 3 | | 5 | | 6 | | 7 | | 8 | |
| Drug | Cage | No. | Dead | (%) | Dead | (%) | Dead | (%) | Dead | (%) | Dead | (%) | Dead | (%) |
| Ps. Boston | | | | | | | | | | | | | | |
| Control | A | 5 | 5 | (100) | 5 | (100) | 5 | (100) | 5 | (100) | 5 | (100) | 5 | (100) |
| Topical AgSD | B | 5 | 2 | (40) | 3 | (60) | 3 | (60) | 3 | (60) | 3 | (60) | 4 | (80) |
| Ps. Mangalore | | | | | | | | | | | | | | |
| Control | C | 4 | 4 | (100) | 4 | (100) | 4 | (100) | 4 | (100) | 4 | (100) | 4 | (100) |
| Topical AgSD | D | 4 | 1 | (25) | 1 | (25) | 2 | (50) | 3 | (75) | 3 | (75) | 3 | (75) |
| 5% Sulfamylon in Marion Base[1] | E | 4 | 4 | (100) | 4 | (100) | 4 | (100) | 4 | (100) | 4 | (100) | 4 | (100) |
| 1% Sulfamylon in Silvadene | F | 4 | 1 | (25) | 1 | (25) | 2 | (50) | 2 | (50) | 2 | (50) | 2 | (50) |
| 30mM/kg carboxylic acid | G | 5 | 0 | (0) | 0 | (0) | 0 | (0) | 0 | (0) | 0 | (0) | 0 | (0) |
| 30mM/kg silver salt of carboxylic acid | H | 5 | 0 | (0) | 0 | (0) | 0 | (0) | 0 | (0) | 0 | (0) | 0 | (0) |
| 6mM/kg silver salt of carboxylic acid | I | 4 | 0 | (0) | 0 | (0) | 0 | (0) | 0 | (0) | 1 | (25) | 2 | (50) |

[1]Cream used in Silvadene; see footnote 2.
[2]Trademark for silver sulfadiazine with a cream carrier manufactured and sold by Marion Laboratories, Inc., Kansas City, Missouri 64137.

TABLE III

Weights of Rats Showing Results of Topical Therapy with Various Compositions

| Topical Agents | Days Post Burn | | | | | | | | | | |
|---|---|---|---|---|---|---|---|---|---|---|---|
| | 1 | 3 | 5 | 7 | 9 | 11 | 13 | 15 | 17 | 18 | 21 |
| Control #1 | 195 | 163 | —[1] | — | — | — | — | — | — | — | — |
| Control #2 | 193 | 159 | — | — | — | — | — | — | — | — | — |
| Control #3 | 201 | 172 | — | — | — | — | — | — | — | — | — |
| Ag Sulfadiazine #1 | 202 | 181 | 150 | — | — | — | — | — | — | — | — |
| Ag Sulfadiazine #2 | 194 | 178 | 148 | — | — | — | — | — | — | — | — |
| Ag Sulfadiazine #3 | 194 | 166 | — | — | — | — | — | — | — | — | — |
| Silver Salt #1 | 202 | 191 | 189 | 203 | 205 | 212 | 203 | 202 | 210 | 206 | 207 |
| Silver Salt #2 | 194 | 187 | 190 | 198 | 200 | 210 | 212 | 215 | 217 | 210 | 216 |
| Silver Salt #3 | 195 | 190 | 183 | 191 | 197 | 200 | 218 | 219 | 223 | 225 | 225 |
| Ag Salt + AgSD #1 | 207 | 200 | 203 | 192 | 188 | 206 | 210 | 214 | 214 | 215 | 226 |
| Ag Salt + AgSD #2 | 195 | 190 | 193 | 196 | 200 | 209 | 213 | 218 | 223 | 216 | 217 |
| AG Salt + AgSD #3 | 193 | 193 | 199 | 207 | 213 | 220 | 219 | 219 | 223 | 218 | 224 |

[1]Dashed lines indicate rats died.

TABLE IV

Topical Therapy of Burned Mice Infected with Ps. 181

| Topical Agents | Concentration | % Mortality (Days P.B.) | |
|---|---|---|---|
| | | 2 | 7 |
| None | — | 80 | 100 |
| Silver Salt | 3mM | 100 | 100 |
| Silver Salt | 6mM | 20 | 100 |
| Silver Sulfadiazine and Silver Salt | 1.0% 3mM | 0 | 0 |
| Silver Sulfadiazine and Silver Salt | 1.0% 6mM | 0 | 0 |
| SILVADENE | 1.0% | 40 | 100 |

Although emphasis has been placed in this disclosure on the combination of QC and its metal salts MeQC in combination with AgSD, other metal salts of sulfadiazine (SD) may be employed in association with or in place of AgSD, such as zinc sulfadiazine ZnSD and/or cerium sulfadiazine CeSD.

Further, in compositions in accordance with this invention, the metal salts of sulfadiazine, such as silver sulfadiazine, and QC and the metal salts MeQC may be such that the metal salt of sulfadiazine, such as silver sulfadiazine, is present in a concentration greater than its effective minimum antimicrobial level, whereas the concentration of QC and MeQC is present in a concentration below its effective minimum antimicrobial level. Moreover, in the compositions in accordance with this invention, QC and the metal salt MeQC may be present in a concentration greater than its effective minimum antimicrobial level and the metal salt of sulfadiazine, such as silver sulfadiazine, may be present in a concentration less than its effective antimicrobial level.

What is claimed is:

1. A composition useful in burn therapy which comprises about 3 mM silver salt of 1-ethyl-6-fluoro-1,4-dihydro-4-oxo-7-(1-piperazinyl)-3-quinoline carboxylic acid, about 30 mM silver sulfadiazine, and a physiologically acceptable carrier.

2. A method of treating burns in animal or man which comprises topically applying the composition of claim 1 to the affected surface.

* * * * *